US005772961A

United States Patent [19]

Mico

[11] Patent Number: 5,772,961

[45] Date of Patent: Jun. 30, 1998

[54] DEVICE FOR USE IN DIAGNOSIS

[75] Inventor: Philip Rees Mico, Malvern Wells, England

[73] Assignee: Bio-Diagnostics Limited, Upton-Upon-Severn, England

[21] Appl. No.: 676,332

[22] PCT Filed: Jan. 18, 1995

[86] PCT No.: PCT/GB95/00086

§ 371 Date: Oct. 10, 1996

§ 102(e) Date: Oct. 10, 1996

[87] PCT Pub. No.: WO95/19845

PCT Pub. Date: Jul. 27, 1995

[30] Foreign Application Priority Data

Jan. 22, 1994 [GB] United Kingdom .................. 9401219

[51] Int. Cl.[6] .................................................. G01N 33/48

[52] U.S. Cl. ............................................. 422/50; 422/61

[58] Field of Search ................................. 422/56, 58, 61

[56] References Cited

U.S. PATENT DOCUMENTS

| | | | |
|---|---|---|---|
| 4,128,692 | 12/1978 | Reid | 428/378 |
| 4,239,853 | 12/1980 | Bradley | 422/61 |
| 4,635,488 | 1/1987 | Kremer | 422/59 |
| 5,110,727 | 5/1992 | Oberhardt | 422/58 |
| 5,182,191 | 1/1993 | Fan et al. | 422/57 |
| 5,196,302 | 3/1993 | Kidwell | 435/4 |
| 5,200,321 | 4/1993 | Kidwell | 435/7.9 |
| 5,244,630 | 9/1993 | Khalil et al. | 422/52 |
| 5,435,970 | 7/1995 | Mamenta et al. | 422/58 |

FOREIGN PATENT DOCUMENTS

| | | |
|---|---|---|
| 0 418 765 | 3/1991 | European Pat. Off. . |
| WO 88/05912 | 8/1988 | WIPO . |
| WO 90/04376 | 5/1990 | WIPO . |
| WO 92/08972 | 5/1992 | WIPO . |
| WO 93/23755 | 11/1993 | WIPO . |

*Primary Examiner*—Lyle A. Alexander
*Attorney, Agent, or Firm*—Young & Thompson

[57] ABSTRACT

A diagnostic device comprises a container formed from a base element (10) and a cover element (11) bonded together to define a cavity. The cover element is formed with an aperture (17) surrounded by a depression (18) and a single or multi-layer porous support membrane (9) located within the cavity so as to be accessible through the aperture. A body of fluid-absorbent material (14) is also located within the cavity in contact with the porous support. The fluid-absorbent material (14) is formed at least partly from fibers of a kind which absorb fluid into the fiber itself, so as to cause the fiber to swell and increase in volume. Appropriate reactants are applied to the porous support (9) so that when a sample to be tested is applied to the support through the aperture (17) the result of any reaction can be observed. Samples or reactants in the form of fluids pass through the porous support and are absorbed by the underlying body (14) of fluid-absorbent material. The composition and arrangement of the fluid-absorbent material may be varied to control the flow of fluid into and through the material. A rubber panel may be located adjacent the fluid-absorbent material to vary the fluid flow rate. A neutralizing agent (23) may be located in the cavity to neutralize fluids used in the test.

10 Claims, 2 Drawing Sheets

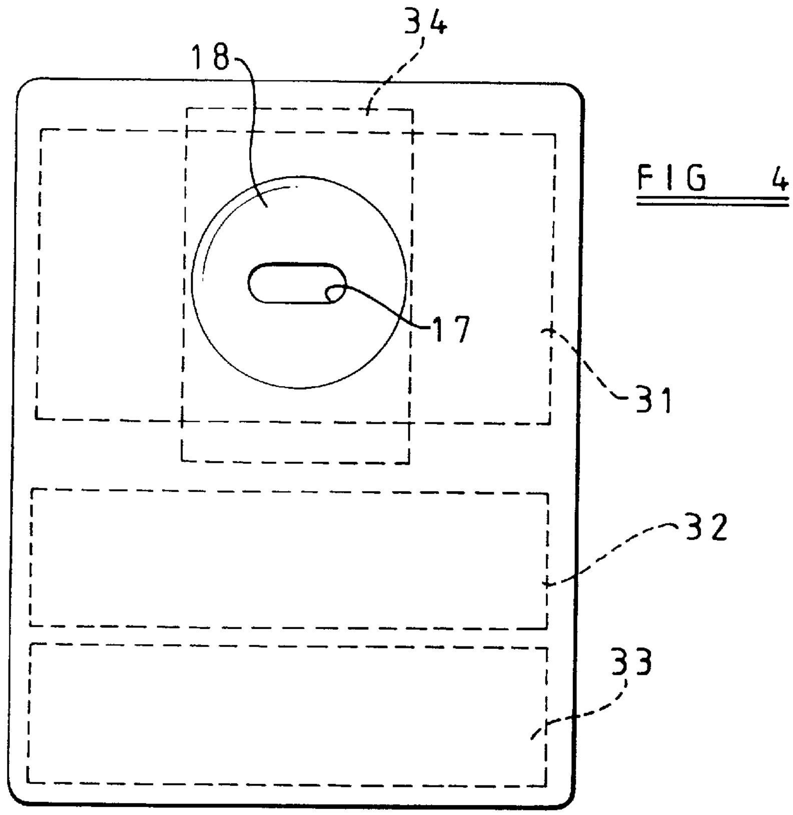
FIG 4
FIG 5
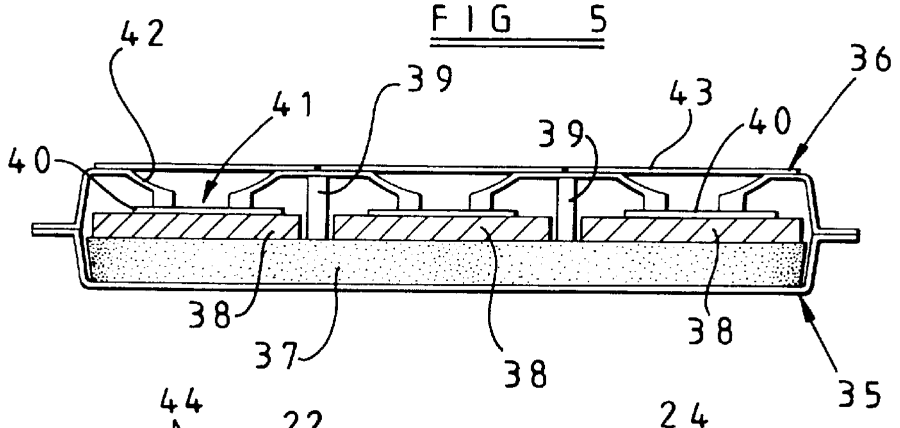
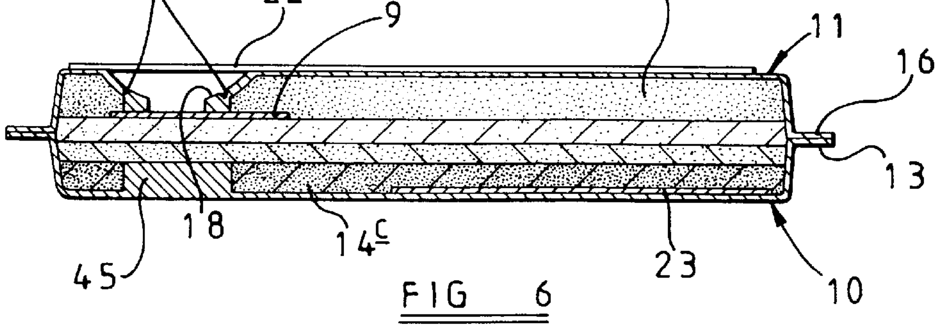
FIG 6

DEVICE FOR USE IN DIAGNOSIS

BACKGROUND OF THE INVENTION

The invention relates to a diagnostic device of a kind which is particularly, but not exclusively, for use in the diagnosis of disease, for example autoimmune diseases. However, the device may also be used in the detection of contaminants, such as bacteria or other extraneous matter, in a sample and may thus be used, for example, in detecting contamination in foodstuffs.

Many diseases, such as autoimmune diseases, may be diagnosed by detecting the presence of the relevant antibodies in the patient's serum. In general terms the presence of the antibodies may be detected by treating the patient's serum with one or more reactants selected to produce a colour reaction which is related to the amount of antibodies present in the sample. The present invention relates to a diagnostic device suitable for use in carrying out tests of this general nature.

The nature of the reactants and the reactions involved do not form a part of the present invention and will not therefore be described in detail, since the precise details of such tests will be known to those skilled in this area.

Diagnostic tests of the general nature referred to are often carried out by adding the sample to be tested to reactants in liquid form and noting colour changes in the liquid, or by applying the sample to a solid support to which the appropriate reactant or reactants have been bound and noting the colour change, if any, on the surface.

For example, one form of diagnostic device comprises a container defining an internal cavity accessible through an aperture in the container. A porous support is located within the cavity so that at least a portion thereof is accessible through the aperture, and a body of fluid-absorbent material is also located within the cavity in contact with the porous support. A test is carried out by applying a sample to the portion of the porous support which is accessible through the aperture. Both the sample and the necessary reactants may be applied to the support through the aperture, or the support may be already pre-treated with the appropriate reactants so that it is merely necessary to apply the sample through the aperture. Depending on the nature of the reaction between the sample and the reactants, any colour change occurring on the support may be observed and will give the appropriate indication of the presence or otherwise in the sample of the antigen, antibody or contaminant which the test is seeking to detect. Liquid samples or reactants applied to the support pass through the support, due to its porosity, and are absorbed by the underlying body of fluid-absorbent material.

By locating the support and fluid-absorbent material within a sealed cavity the materials, and any reactants which they may carry, are protected from contamination at all times prior to use and the device may conveniently be stored and transported without any further packaging. Also, after use of the device in a diagnostic test, the substances involved in the test are retained on the fluid-absorbent material within the device which makes for convenient storage and disposal.

In known devices of this type, the fluid-absorbent material normally comprises cellulose fibres, glass fibres, or similar fibrous material where the fibres are not themselves fluid-absorbent but where absorption of the fluid into the body of material is effected by capillary action and the flow of fluid in and along the spaces between adjacent fibres. The composition of the material is usually substantially uniform and there is therefore no significant control of the rate of flow of fluid from the porous support into and through the underlying body of fluid-absorbent material.

SUMMARY OF THE INVENTION

According to one aspect of the present invention, there is provided a novel form of diagnostic device where the body of fluid-absorbent material is of such a kind that the rate of flow of fluid into and through the body of material can be controlled by varying the composition and arrangement of the material.

According to this aspect of the invention there is provided a diagnostic device comprising a container defining an internal cavity, at least one aperture in the container, a porous support located within the cavity so as to have at least a portion thereof accessible through said aperture, and a body of fluid-absorbent material located within the cavity adjacent the porous support, said body of fluid-absorbent material being formed from fibres at least some of which are super absorbent fibres of a kind capable of absorbing fluid into the material of the fibre itself, so as to cause the fibre to swell and increase in volume.

Preferably said super absorbent fibres form only a proportion of the body of fluid absorbent material, the remainder of the body of material being formed from other fibres which are not themselves capable of absorbing material into the material of the fibre itself, or which are less fluid-absorbent than said super absorbent fibres.

The inclusion of super-absorbent fibres in the body of fluid-absorbent material provides fast fluid uptake in the material, and by varying the proportion and size of super absorbent fibres in the material, the rate of flow of fluids into and through the material may be varied according to the nature of the test being carried out. For example, in some cases it may be desirable to retard the absorption of fluids to allow sufficient time for the reaction to take place.

Said body of fluid-absorbent material may comprise a plurality of layers of material so disposed that fluid applied to said porous support is absorbed into the layers in succession, passing through one layer to reach the next adjacent layer.

The proportions of super absorbent fibres in the respective layers may differ from one layer to another so that the layers are of different absorbencies. For example, the layers may be of increasing absorbency as they extend away from the porous support.

By increasing the absorbency with distance from the porous support, a fluid gradient is created which may provide a controlled rate of fluid flow with the final layer of absorbent material drawing fluid away from the porous support at a rate such as to provide a substantially constant saturation level in the absorbent body, thus providing greater uniformity of flow. This arrangement may ensure that there is no spillage of reactants and no disturbance of the test site on the porous support, and may allow the use of comparatively large volumes of reactants. Also, the majority of the fluids are eventually absorbed into the most absorbent layer, thus providing a controlled site for neutralisation of the fluids within the device, if required.

In any of the above arrangements said super absorbent fibres may comprise a cross-linked acrylate copolymer in fibre form.

Said container may comprise a base element and a cover element bonded to the base element so as to define said cavity, said aperture being formed in the cover element and a removable cover being provided for sealing engagement across said aperture.

A portion of the cover element, surrounding and including said aperture, may be detachable from the rest of the container, together with at least a portion of said porous support which is visible through said aperture. This arrangement allows the test site to be stored separately from the rest of the device for record purposes and subsequent checking.

The detachable portion of the cover element may be connected to the rest of the container by a region of weakness which may be ruptured to detach the portion from the container. The container may then be formed with a punch element which may be displaced into engagement with said detachable portion so as to rupture said region of weakness.

Usually, in the case where the porous support is pre-treated with a reagent, the reagent covers only a small area of the exposed portion of the porous support. Consequently, a large proportion of the sample or other fluids applied to the support may pass through the support and into the underlying fluid-absorbent body without reacting with the reagent. As much as 90% of the fluids may bypass the reagent in this manner. The invention therefore also provides an arrangement whereby substantially all of the fluids applied to the porous support react with the reagent.

Accordingly, the invention provides an arrangement where the portion of said porous support which is accessible through said aperture in the container includes at least one porous area for reception of a reactant, the remainder of said portion of the support, around said area, being rendered substantially non-porous by application of a blocking material.

The blocking material may be selected from surfactants, proteins, latex particles, fats, fatty acids, carbohydrates or any other suitable materials.

In any of the arrangements according to the invention the container may comprise a base element and a cover element bonded to the base element so as to define said cavity, each element comprising a panel of rigid or semi-rigid material shaped to define said cavity or part of said cavity. The cavity or part cavity on one element may be surrounded by a continuous border surface which is bonded to a corresponding surface on the other element.

Preferably the cover element and base element are of similar contour so that the cover element overlies substantially all of the base element. Preferably the two elements are bonded together around their peripheries to form a substantially air-tight seal.

In any of the above arrangements the aperture in the container is preferably surrounded by a depression on the outer surface of the container to assist in guiding a fluid to be tested to the aperture. The porous support may comprise a plurality of superimposed porous membranes.

The container may include a neutralising material located to neutralise a fluid absorbed by least a part of said body of fluid-absorbent material.

The invention also provides a diagnostic device comprising a container defining an internal cavity, at least one aperture in the container, a porous support located within the cavity so as to have at least a portion thereof accessible through said aperture, and a body of fluid-absorbent material located within the cavity and in contact with the porous support, a portion of the container, surrounding and including said aperture, being detachable from the rest of the container, together with at least a portion of said porous support which is visible through said aperture.

The invention further provides a diagnostic device comprising a container defining an internal cavity, at least one aperture in the container, a porous support located within the cavity so as to have at least a portion thereof accessible through said aperture, and a body of fluid-absorbent material located within the cavity and in contact with the porous support, the portion of said porous support which is accessible through the said aperture including at least one porous area for reception of a reactant, the remainder of said portion of the support, around said area, being rendered substantially non-porous by application of a blocking material.

BRIEF DESCRIPTION OF THE DRAWINGS

FIG. 4 is a diagrammatic plan view of the device, showing another feature of the invention, and FIGS. 5 and 6 are diagrammatic cross-sections through alternative forms of device.

DESCRIPTION OF THE PREFERRED EMBODIMENTS

Figure 1:
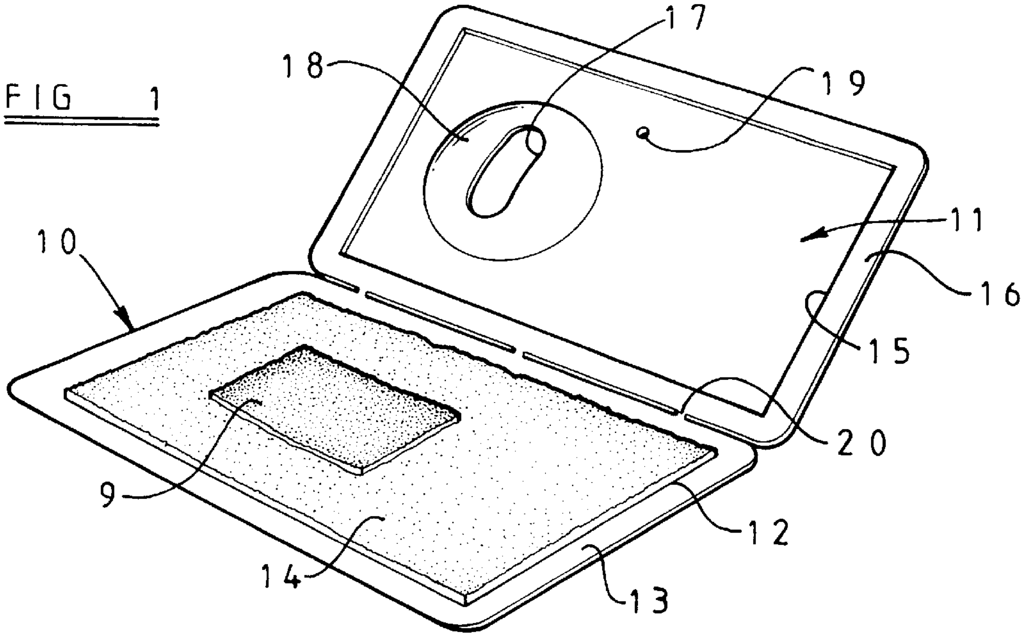
FIG. 1 is a diagrammatic perspective view showing the major components of one form of diagnostic device prior to assembly.

Referring to FIG. 1, the diagnostic device comprises a generally rectangular base element 10 and a similarly shaped and dimensioned cover element 11. The base element 10 comprises a rectangular depression 12 surrounded by a peripheral flange 13. Located in the depression 12 is a correspondingly shaped pad 14 of fluid-absorbent material, the nature of which will be described in greater detail below. The thickness of the pad 14 is somewhat greater than the depth of the depression 12.

Figure 2:
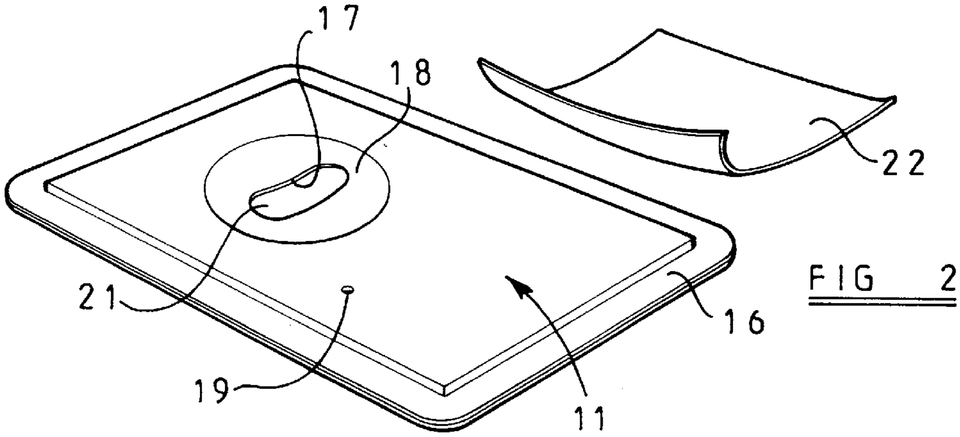
FIG. 2 is a perspective view of the assembled device.

The cover element 11 is also formed with a rectangular depression 15 surrounded by a peripheral flange 16. In addition the cover element 11 is formed with an oblong, rounded-end aperture 17 surrounded by a circular generally bowl-shaped depression 18 which is convex as seen in FIG. 1 and concave as seen in FIG. 2. A small hole 19 is also formed in the cover element 11, a short distance from the aperture 17.

Between the upper surface of the pad 14 and the aperture 17 is a smaller panel 9 of porous material, such as nitrocellulose membrane material, which is to serve as a support for the reactants used in the diagnostic test. The panel 9 is preferably ultra-sonically bonded to the underside of the cover 11, around the aperture 17, as indicated at 8 in FIG. 3. A further layer of fluid-absorbent material 24 may be applied over the pad 14 and support 9, being formed with an aperture to expose a portion of the support. The support 9 may comprise a single layer or may comprise a plurality of superimposed porous membranes.

Figure 3:
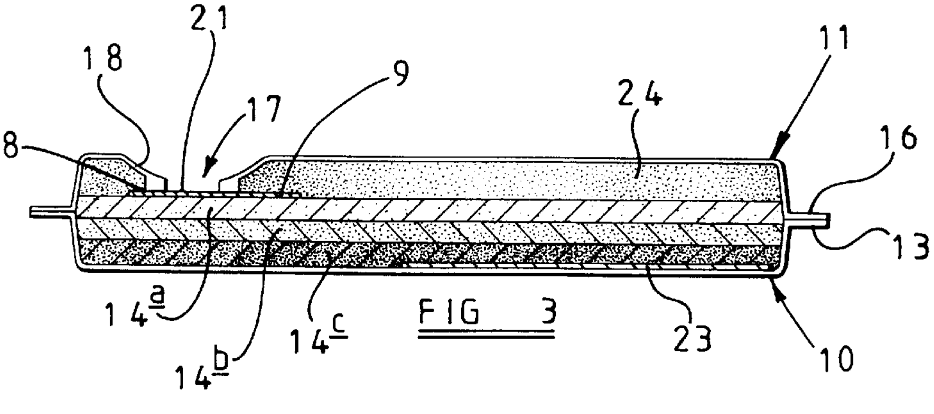
FIG. 3 is a cross-section through the assembled device.

The base element 10 and cover element 11 are moulded from suitable plastics material. They may be separately formed or, as shown in the drawings, may be moulded in one piece. In this case, as shown, the adjacent edges of the two elements are integrally connected by a number of connecting tabs 20 spaced apart along the common edges. The arrangement allows the cover element 11 to be folded over so as to overlie the base element 10, the fluid-absorbent pad 14 and support 9 then being contained within the cavity formed by the two depressions 12 and 15. FIGS. 2 and 3 show the folded over position, and it will be seen that an oblong surface portion 21 of the support 9 is exposed and accessible through the aperture.

As mentioned above, the support 9 is ultra-sonically bonded to the underside of the cover element 11, around the aperture 17, prior to assembly of the base 10 and cover 11. This provides an air-tight seal between the support 9 and the cover, around the aperture 17. Alternatively, the support may be bonded to the cover by an adhesive.

Various methods may be employed for sealing the cover element to the base element. In each case the overlying peripheral flanges 13 and 16 are bonded together. For example, they may be secured together by an adhesive, such as a pressure-sensitive adhesive which is applied to one of the flanges before the cover element is folded over into contact with the base element. Alternatively the flanges may be welded together by thermal welding, ultrasonic welding or any other welding method. Preferably the bonding method is such that the two elements are hermetically sealed together.

In order to complete the sealing of the device both before use and after use, there is provided a flexible sealing label 22 which is shaped and dimensioned to cover both the aperture 17 and the hole 19. The label 22 may comprise latex rubber impregnated paper which may be printed with identifying, instructional or other material. Over the print is applied a protective clear glossy layer of polyester or vinyl, and an additional laminate of transparent polyester may optionally be applied over the first polyester or vinyl layer. The underside of the label 22 is coated with a pressure sensitive adhesive such that it may be applied to the cover element 11 and removed therefrom several times if required, each time providing complete sealing of the aperture 17 and hole 19. Preferably the laminated sealing label has extremely low air permeability transfer to maintain a stable internal gaseous environment within the device.

Before use of the device the label 22 extends across the front of the cover element 11 of the device so as to seal the aperture 17 and hole 19. A rectangular portion of the label which extends across the depression 18 may be perforated or slit along one or more edges so that the portion may be peeled off the cover 11, so as to reveal the test site without removing the rest of the label. In use of the device this portion of the label is first peeled off to reveal the depression 18, the aperture 17 and the visible portion 21 of the porous support 9 which is exposed in the aperture.

The sample of the patient's serum, or antigen sample, to be tested is then applied to the visible portion 21 of the support 9. The appropriate reactant may also be applied to the visible portion 21 of the support 9 or, alternatively or additionally, the support may be pre-impregnated with the appropriate reactant. Whichever is the case, the resulting colour changes occurring on the visible portion 21 of the support may be observed and analysed, for example by comparison with standard colour charts indicating the presence of antibodies. The hole 19 serves to equalise the pressure between the interior and the exterior of the device as fluids are applied to the pad and the reactions occur.

After use of the device the detached portion of the label 22 is resealed over the aperture 17 and hole 19 so that the device may be safely disposed of or stored for future reference. The portion of the label overlying the aperture is preferably transparent so that the condition of the porous support can still be seen after the portion of the label has been reapplied. Alternatively, the device may be constructed, as will be described below, so as to allow removal of the test site, i.e. the portion of the device containing the support 9, so as to form a module containing a permanent record of the reaction, such record also including test data, date or other information. The resulting hole or cavity which is left following removal of the test site for permanent record may be resealed by reapplying the detached portion of the label 22 or by applying a new label or other sealing device.

The fluid absorbent pad 14 is formed from fibres and may be formed from a single type of fibre or a mixture of different fibres. However, in accordance with one aspect of the present invention at least one of the fibres in the pad is a fibre of a kind which absorbs fluid into the material of the fibre itself so that the fibres swell and increase in volume as fluid is absorbed. Fibres of this description are referred to as "super absorbent fibre", or "SAF". The SAF may, for example, be a cross-linked acrylate copolymer, partly neutralised to the sodium salt, in fibre form, but any other similarly acting fibre material may be employed.

The fibres may have a length in the range from 6–60 mm and a diameter in the range of 10–100 micron, and preferably have the capacity to increase in diameter many times, for example 5–30 times, with fluid absorption.

As previously explained, such fibres differ from the cellulose or glass fibres hitherto used in diagnostic devices of this general type in that fluids are absorbed by the fibres themselves instead of being absorbed into the pad by capillary action between adjacent fibres. Where only a proportion of the fibres in a pad are super-absorbent fibres, the absorbency of the pad may be controlled and varied by adjusting the proportion of super-absorbent fibres in the pad, or by adjusting the size, i.e. length and/or diameter, of the fibres.

As shown in FIG. 3, the pad 14 may comprise a number of layers 14*a*, 14*b*, 14*c*, of different degrees of absorbency, the layers further from the support 9 being of greater fluid absorbency than layers nearer the support. The purpose of the pad 14 is to draw fluid away from the reaction site on the support 9, and the multi-layer arrangement improves the tendency for fluids to be retained in the pad 14 and prevents reflux of fluid at the aperture 17.

Thus, the layer 14*a*, adjacent the support 9 may have a low proportion of super-absorbent fibre, for example 20–40%. The intermediate layer 14*b* may have a medium SAF content, for example 30–50%, and the layer 14*c* furthest from the support 9 may have a high SAF content, for example 50–60%. The remainder of each layer may comprise other fibres, or a mixture of fibres, such as cellulose or glass fibres, which do not themselves absorb fluid into the fibres. Alternatively, the other fibres may be of a kind which absorb fluid into the material of the fibres, but which are substantially less fluid-absorbent than said super absorbent fibres.

The fluid-absorbent pad may typically have a length of 67.82 mm, a width of 47.92 mm and an overall thickness of 2.74 mm. The volume of the dry pad is then approximately 8.90 $cm^3$, but after absorption of fluid the volume of the wet pad may be of the order of 21.57 $cm^3$.

A typical construction of each layer of a multi-fibre pad would be SAF in addition to a bi-component fibre such as that available under the name DANAKLON E-SC, together with a fluff pulp. The bi-component fibre provides binding strength, bulking and texture, whereas the fluff pulp helps provide a pad with high pad integrity. The pads may be compacted or not compacted, according to the demands of the device.

In a typical construction the low absorption pad 14*a* adjacent the test site may have the following composition:

50% fluff pulp

25% DANAKLON

25% SAF the intermediate layer 14_b_ may have the following composition:

42% fluff pulp

18% DANAKLON

40% SAF and the layer 14_c_ furthest from the test site may have the following composition:

25% fluff pulp

15% DANAKLON

60% SAF

With a low SAF content in the uppermost layer 14_a_ the rate of flow through that layer is rapid but the retention of fluid in the layer is comparatively small. In the layer 14_c_ of high SAF content, however, the flow rate through the layer is reduced and there is a high degree of retention of fluid within the layer 14_c_.

Accordingly, by varying the SAF content of the layers, and also by varying the size of the layers and of the fibres of which they are comprised, variation in flow rates through the layers can be closely controlled. In this way, the time allowed for reactants to conjugate at the reaction site can also be controlled, so that the specificity and sensitivity of the device can be optimised.

For example, the composition of the layers may be selected so that the rate of passage of a test sample or reactant through the test site can be uniform, improving sensitivity. Also, the proportions of SAF in the layers can be arranged to cause very rapid removal of reactants from the test site. In the case of some reactants, such as calorimetric reagents, this allows for reduction of background staining and facilitates differentiation of borderline positives/negatives, thus improving sensitivity and discrimination.

The layers 14_a,_ 14_b_ and 14_c_ may comprise separately formed layers laid one upon another within the device, or may comprise different regions of a single thicker pad, the different regions being of different compositions.

Where the pad 14 comprises a number of layers there may be provided between the layers rings or strips of rubber material or other adhesive (not shown) to direct fluids away from the aperture 17. In this way reactants are removed rapidly from the test site and this allows for the reaction to proceed without further interference when further reactants are placed on the test site. Alternatively, parts of the different layers may be ultrasonically welded together to provide for fluid passage and tracking.

During manufacture of the device the support 9 may be pre-impregnated with small volumes of reactants by passing the supports, or open devices, successively past airbrush or inkjet devices, or other dispensing pumps or systems, for applying the small volumes of fluid which are subsequently dried so as to be bound to the support. The filling of the device may be carried out in the presence of inert or other gases such as nitrogen, oxygen, hydrogen or carbon dioxide, to assist in stability of the reactants enclosed.

The cavity within the device may also incorporate biocidal chemicals, virological, bacteriological or other neutralising materials, indicated at 23 in FIG. 3, such as to render the interior of the device inactive or harmless after completion of the diagnostic tests. In cases where the neutralisation material requires activation through application of a further fluid, however, the further fluid may be applied to the exposed portion 21 of the support 9 either separately or as a fluid mixed with one of the reactants.

The neutralising materials 23 in the device may be incorporated within the cavity by various means. For example they may take the form of solid elements, such as freeze-dried elements, a reticulated foam filled with the appropriate materials, electrostatically absorbed materials, chemical solutions absorbed into fibrous material, gel suspensions, colloids or other systems.

It has also been found that the flow rates of fluids through the absorbent pad 14 may be varied and controlled by placing a thin layer of rubber 23 (for example Challis 0.1–2 mm) or other similar composite materials within the device and beneath the absorbent pad. It is believed that the effect of the rubber is to modify the electrostatic charge on the support 9, and by positioning the rubber or similar material close to or distant from the test site different flow rates can be established. By careful selection and shaping of the rubber layers, further control of sensitivity of the device can be achieved.

FIG. 4 is a plan view of the device of FIGS. 1–3 showing diagrammatically at 31, 32, 33 and 34 respectively typical alternative positions for the positioning of a thin panel of rubber beneath the absorbent pad. Tests made using rubber panels at these sites, as well as using an all-over rubber panel or no rubber panel, produce the following results:

| Position of Rubber | Position 31 | Position 32 | Position 33 | Position 34 | All-over Panel | No Panel |
|---|---|---|---|---|---|---|
| Flow-rate secs/ml | 114.40 | 121.60 | 129.80 | 130.60 | 168.00 | 127.66 |

These results suggest that a rubber panel of the size and position indicated at 31 or 32 will increase the rate of flow of fluid through the absorbent pad, when compared to a device with no rubber panel, whereas all the other positions and sizes of rubber panels cause a reduction in flow-through times.

Although the device shown in FIGS. 1–4 is formed with only a single aperture, two or more apertures may be provided, if desired, providing access to different portions of the support 9 and pad 14, or access to different supports or pads in different cavities in the device. This enables multiple tests to be carried out or control fluid sites to be employed.

FIG. 5 is a diagrammatic cross-section through such a multiple test device. In this case there is provided within the base element 35 a single lower reservoir pad 37 on top of which are placed three separate fluid-absorbent pads 38 separated from one another by dividing strips 39. As in the arrangement of FIGS. 1–3, each pad 38 may comprise a number of layers of different absorbencies. As before the layers may be separate or may comprise different regions of an integral pad.

Bearing on each fluid-absorbent pad 38 is a porous support membrane 40 of nitro-cellulose or other suitable material. As in the previously described arrangement, each support membrane 40 is preferably ultra-sonically welded to the cover element 36.

The cover element 36 is formed with three oblong, rounded-end apertures 41 each surrounded by a circular generally bowl-shaped depression 42. Flexible sealing labels 43, similar to the label 22 of FIG. 2, are applied to the cover element 36 over the depressions 42 respectively. The labels 43 may be separate labels or may comprise different perforated sections of an overall single label.

The overall reservoir pad 37 has a greater SAF content than the absorption pads 38 and therefore fluid tends to be retained in the pad 37 to prevent reflux of fluid from the pad to any of the test sites, or transfer of fluid from one test site to another.

As previously mentioned, the device according to the invention may be so constructed as to allow removal of the test site, so as to form a module containing a permanent record of the reaction. One such arrangement is shown in FIG. 6.

The basic device is similar to that shown in FIGS. 1 to 3, and the same reference numerals therefore refer to corresponding parts. In this form of the device, however, a ring of the material of the cover element 11, around the test site, is weakened as indicated at 44, for example by thinning of the material of the cover element in this region. Opposite the test site the bottom wall of the base part 10 is integrally formed with an upstanding circular punch button 45 of similar diameter to the ring 44. The button 45 is received within a corresponding circular aperture in the lowermost layer 14*c* of the fluid-absorbent pad 14.

After the test has been completed, the label 22, or tear-off portion thereof, is replaced over the depression 18 as shown in FIG. 6. The device is then held between thumb and forefinger at the position of the button 45 and depression 18, and the cover element and base element 10 are squeezed together in this region. The button 45 punches out a circular portion of the support 9 and also detaches the central portion of the depression 18, within the weakened ring 44, pushing these elements towards the underside of the label 22 so that they adhere to the adhesive on the underside of the label. The label 22, or portion thereof, is then detached carrying with it the circular portion of the support 9 attached to the circular portion of the cover element 11. After drying, the label 22, together with the test area, may be attached to a record card containing details of the test, or the remainder of the label 22 may be folded over to enclose the circular portion of the support 9. The portion of the label above the test site is preferably transparent so that the test site can be seen without removing the label.

In any of the above arrangements the device is preferably totally sealed from the outside environment, in air-tight manner, so that internally it can be controlled for relative humidity and gaseous control. Relative humidity can be controlled both in the filling or closing environment, as well as by inclusion of a desiccant tablet or pack within the device.

Nitrogen is a common stabilising gas used to control breakdown of biological and chemical reactants, and the interior of the device may therefore be filled with nitrogen during manufacture or before resealing, although other gases can be used depending on the nature of the test to be performed.

In the case where a reactant is pre-applied to the test area, usually in the form of a thin line or dot of reactant, it is advantageous if the majority of the test sample can be exposed to the test site. However, usually only 10–20% of the exposed area of the support membrane bears the reactant antibody or antigen so that the majority of the sample passes through the membrane without having been in contact with the reactant.

In order to increase the proportion of the sample which reacts with the reactant, the time for which the fluid sample is held in the depression over the test site may be increased, and this may be achieved by controlling the rate of fluid flow through the membrane and into the absorbent pad, as previously described. Alternatively, however, the exposed area of the membrane which does not bear reactant may be masked by blocking materials, which may be surfactants, proteins, latex particles, fats, fatty acids, carbohydrates or other organic or inorganic chemicals. In the case of surfactants or other blocking chemicals, which may vary the electrostatic charge or hydrophobicity of the support membrane, these may be applied by selective spraying or masking. In the case of latex particles these can be made to adhere selectively and independently to the non-test areas. In this way, sensitivity of the test can be dramatically increased, or conversely less reactant may be employed.

I claim:

1. A device for use in testing samples comprising a container defining an internal cavity, at least one aperture in the container, a porous support located within the cavity so as to have at least a portion thereof accessible through said aperture to provide a visual indication of test results, and a body of fluid-absorbent material located within the cavity adjacent the porous support, said body of fluid-absorbent material being formed from fibres at least some of which are super absorbent fibres of a kind capable of absorbing fluid into the material of the fibre itself, so as to cause the fibre to swell and increase in volume, said container comprising a base element and a cover element which overlies substantially all of the base element and is bonded to the base element around its periphery so as to define said cavity, each element comprising a panel of rigid or semi-rigid material shaped to define said cavity or part of said cavity, the cavity or part cavity on one element being surrounded by a continuous border surface which is bonded to a corresponding surface on the other element to form a substantially air-tight seal, the aforesaid aperture being formed in the cover element of the container and being surrounded by a depression on the outer surface of the cover element to assist in guiding a fluid to the aperture, and a removable cover being provided for sealing engagement across both said aperture and depression, wherein the cavity in the container also includes a panel formed of rubber which is located adjacent the body of fluid-absorbent material to vary the rate of flow of fluid through said material.

2. A device according to claim 1, wherein said body of fluid-absorbent material comprises a plurality of layers of material so disposed that fluid applied to said porous support is absorbed into the layers in succession, passing through one layer to reach the next adjacent layer.

3. A device according to claim 1, wherein said super absorbent fibres comprise a cross-linked acrylate copolymer in fibre form.

4. A device according to claim 1, wherein the portion of said porous support which is accessible through said aperture in the container includes at least one porous area for reception of a reactant, the remainder of said portion of the support, around said area, being rendered substantially non-porous by application of a blocking material selected from surfactants, proteins, latex particles, fats, fatty acids or carbohydrates.

5. A device according to claim 1, wherein said porous support comprises a plurality of superimposed porous membranes.

6. A device according to claim 1, wherein the cover element and base element are each formed with an outwardly projecting peripheral flange, the peripheral flanges being bonded together to form said substantially air-tight seal.

7. A device according to claim 6, wherein said peripheral flanges are bonded together by ultra-sonic welding.

8. A device according to claim 1, wherein a portion of the cover element, surrounding and including said aperture and depression, is detachable from the rest of the container, together with at least a portion of said porous support which is visible through said aperture.

9. A device according to claim 8, wherein said detachable portion of the cover element is connected to the rest of the container by a region of weakness which may be ruptured to detach the portion from the container.

10. A device according to claim 9, wherein the container is formed with a punch element which may be displaced into engagement with said detachable portion so as to rupture said region of weakness.

* * * * *